(12) United States Patent
Mason et al.

(10) Patent No.: US 6,869,801 B2
(45) Date of Patent: Mar. 22, 2005

(54) ASSESSMENT OF CERVICAL CELLS

(75) Inventors: Robert James Mason, Newmarket (GB); Edward William Pascoe, Huntingdon (GB); Christopher Harold Holmes, Bristol (GB)

(73) Assignee: Smearcheck Limited, London (GB)

( * ) Notice: Subject to any disclaimer, the term of this patent is extended or adjusted under 35 U.S.C. 154(b) by 0 days.

(21) Appl. No.: 09/230,955

(22) PCT Filed: Aug. 5, 1997

(86) PCT No.: PCT/GB97/02108

§ 371 (c)(1), (2), (4) Date: May 4, 1999

(87) PCT Pub. No.: WO98/05967

PCT Pub. Date: Feb. 12, 1998

(65) Prior Publication Data

US 2002/0197723 A1 Dec. 26, 2002

(30) Foreign Application Priority Data

Aug. 5, 1996 (GB) ............................................. 9616429

(51) Int. Cl.$^7$ ........................ G01N 33/50; C07K 16/30; C12P 21/08
(52) U.S. Cl. ..................... 436/64; 530/388.1; 530/388.8
(58) Field of Search ........................... 530/388.1, 388.8; 436/63, 64

(56) References Cited

U.S. PATENT DOCUMENTS

| | | | |
|---|---|---|---|
| 4,666,845 A | * 5/1987 | Mattes et al. | ................ 435/240 |
| 4,714,680 A | 12/1987 | Civin | ..................... 435/240.25 |
| 4,965,204 A | 10/1990 | Civin | ..................... 435/240.27 |

FOREIGN PATENT DOCUMENTS

| | | | | |
|---|---|---|---|---|
| GB | 2 215 046 | 9/1989 | ......... | G01N/33/574 |

OTHER PUBLICATIONS

Eltabbakh et al., Obstetrics and Gynecology, 85(4):499–503, Apr. 1995.*
Kamiya et al., Acta Cytologica, 37(2):131–134, Apr. 1993.*
Smedts, et al., American Journal of Pathology, 142(2):403–412, Feb. 1993.*
Stedman's Medical Dictionary, p. 1456, 24 ed., Williams & Wilkens, Baltimore, 1982.*
The abstract of Buchler et al (Archives of Gynecology, 1983, vol. 233 pp. 121–130).*
Malecha et al (International Journal of Gynecological Pathology, 1992, vol. 11, pp. 24–29).*
Epenetos et al., "Targeting of iodine–123–labelled tumour–associated monoclonal antibodies to ovarian, breast and gastrointestinal tumours," The Lancet, Nov. 6, 1982, 999–1004.
Epenetos, A.A., "Antibody guided lymphangiography in the staging of cervical cancer," Br. J. of Cancer, 51: 805–808 (1985).
Jha et al., "Monoclonal antibodies for the histopathological diagnosis of cervical neoplasia," British Journla of Obstetrics and Gynaecology, 91: 483–488 (1984).
Porta et al., "Diagnosis of cervical carcinoma using the monoclonal antibodies technique," Patologia e Clinica Ostetrica e Ginecologia, 14: 348–355 (1986). (Translation).
Holmes et al., "Expression of a Monoclonal Antibody–Defined Liver–Associated Antigen in Normal Rat Hepatocytes and Hepatocellular Carcinoma Cells," *Int. J. Cancer* 29:559–565 (1982).
Holmes et al., "Application of a Monoclonal Antibody to Rat Hepatocytes in the Study of Rat Liver Carcinogenesis," Publication of the Proceedings of the Th Meeting of the European Association for Cancer Research Budapest, Oct. 12–15, 1981, 471–481.
Holmes et al., "A Monoclonal Antibody Reactive with Human Hepatocytes," *Liver* 3:295–302 (1983).
Holmes et al., "Monoclonal Antibodies Reacting with Normal Rat Liver Cells as Probes in Hepatocarcinogenesis," Cancer Research, 44, 1611–1627 (Apr. 1984).
Prosperi Porta et al., "Diagnosis of Carcinoma of the uterine Cervix with Monoclonal Antibodies Technique," Pat. Clin. Ost. Gin., 14:348–355 (1986). (English Abstract).

* cited by examiner

*Primary Examiner*—Karen A. Canella
(74) *Attorney, Agent, or Firm*—Drinker Biddle & Reath LLP

(57) ABSTRACT

A method of determining premalignant or neoplastic disease state in a tissue sample containing cells of the cervix, the method comprising contacting specific monoclonal antibodies to a cervical tissue sample, determining binding of the antibodies to the sample and comparing the binding with a pattern of binding of the same antibodies to a normal cervical cell sample. Hybridomas which produce suitable antibodies have been deposited at the European Collection of Animal Cell Cultures (ECACC) under the accession numbers ECACC 95020718, 95020716, 95020720, 95020717 and 95020719.

7 Claims, No Drawings

ASSESSMENT OF CERVICAL CELLS

The present invention relates to assessment of cells in a sample of tissue containing cells of the cervix. More particularly, it relates to evaluation of the state of cells of the cervix, discriminating between normality and some deviation from normality, and is generally for use in screening women to detect those whose cervical cells are abnormal. Samples found to be abnormal may be examined in more detail and the condition of cells in the cervix investigated further. Identification of a malignant or pre-malignant condition is typically followed by appropriate treatment following more extensive diagnostic procedures.

Cancer of the cervix is the second most common cancer in women. The current method of detection is the Papanicolau or PAP test, which uses conventional cytological dyes to stain cells in a smear sample, enabling the visual detection of cellular nuclei and cytoplasm with a microscope. Trained personnel make semi-subjective assessments of the normality or otherwise of the cells examined. The PAP test, though universally accepted, is labour-intensive and prone to human error, as evidenced by a number of recent well-publicised scares casting doubt on the accuracy of assessments made by a few of those people who spend their entire day looking at smear samples.

An alternative or more objective way of assessing the state of cells in cervical cell samples would be useful and advantageous. Benefit would be obtained by the removal or at least amelioration of problems arising from the need for subjective, visual evaluation.

It is known that cells within tissues of the mammalian body express cellular markers that are either unique or partially restricted to particular cell populations. Different cell populations may be distinguished by virtue of their individual cell markers. Thus, a cell may be shown to belong to a particular cell population (eg lymphoid cells) because of its expression of markers defining that population.

These cell markers may be various kinds of molecules, including proteins, lipids, carbohydrates and combinations of these, such as glycoproteins, glycolipids and lipoproteins.

It is possible to detect cell markers using binding molecules, such as antibodies, with the requisite specificity. Such binding molecules can be used in qualitative or quantitative detection of cells which bear particular markers and are thus included in a particular cell population.

Holmes et al have described previously a monoclonal antibody able to bind specifically to an antigen on normal hepatocytes within the liver but not able to bind cells other than hepatocytes. No binding could be detected on a number of transplanted and primary dimethylaminoazobenzene-induced hepatomas nor on liver cells from patients with a variety of liver diseases. (See: *Tumour Progression Markers— Proceedings of the Sixth Meeting of the European Association for Cancer Research, Budapest* 12–15 Oct. 12–15, 1981, 471–481 (1982); *Liver* (1983), 3: 295–302; *Int. J. Cancer* (1982), 29: 559–565; *Cancer Research* (1984), 44: 1611–1624.)

The present invention is founded in the realisation that it is possible to recognise a pattern of surface antigens on cells of the cervix which represents normality, such that a deviation from a determined and noted pattern of normality can be perceived. Conveniently, antibodies or other specific binding molecules may be used in the qualitative and/or quantitative detection of marker antigens on the cells, enabling increased or reduced expression or loss of one or more of the markers to be correlated with a disease (or pre-disease) state. In screening, this enables samples with some deviation from normality to be identified and examined further, ie suspect samples are highlighted for further examination by suitably qualified personnel. If abnormality in a particular sample is serious or potentially serious, appropriate steps may be taken to examine and then perhaps treat the woman from whom the sample was obtained. Diagnosis and decisions on the need for and nature of treatment remain the domain of clinicians.

For operation of the present invention it is not necessary for the marker antigens actually employed in the test to be identified. Ultimately, what is important is that a panel of antibodies or other binding molecules is identified as able to bind cervical cells with a pattern which is associated with the cervix being normal, and that deviation of binding of those binding molecules from the pattern of normality is correlated with the onset of pathological conditions. The onset of pathology may then be identified in samples containing cervical cells by some deviation from the established pattern of normality for those particular binding molecules.

This is exemplified by data included herein relating to five monoclonal antibodies able to bind to various cells of the cervix. The pattern of binding of these antibodies to an abnormal tissue sample containing cervical cells is different from the binding to normal cervical samples enabling identification of abnormality. Clearly, other specific binding molecules may be employed successfully in aspects of the present invention as long as the requirements set out in the preceding paragraph are satisfied. Such other molecules may bind the antigens bound by the exemplified antibodies, at the same or different epitopes. Indeed they may bind different antigens altogether.

According to a first aspect of the present invention there is provided a method of determining abnormality in a tissue sample containing cells of the cervix, the method comprising determining binding of antibodies to the sample and comparing the binding with the pattern of binding of said antibodies to a normal cervical cell sample. The pattern of binding of the antibodies to normal cervical cells may, and generally will, be established prior to performance of the method.

The reactivities of antibodies on normal and test samples may be determined by any appropriate means. Tagging with individual reporter molecules is one possibility. The reporter molecules may directly or indirectly generate detectable, and preferably measurable, signals. The linkage of reporter molecules may be directly or indirectly, covalently, eg via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and TEXAS RED®. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

The signals generated by individual antibody-reporter conjugates may be used to derive quantifiable absolute or relative data of the relevant antibody binding in normal and test samples. In addition, a general nuclear stain such as propidium iodide may be used to enumerate the total cell population in a sampled smear, allowing the provision of quantitative ratios of individual cell populations relative to the total cells in a smear, at least where individual antibody reactivities correlate with particular cervical cell populations.

An actual expansion or reduction in the absolute numbers of a particular cell population is not a necessary pre-requisite for the purposes of this invention. Any change in the detection of antibody binding (and by implication change in the phenotypic cell markers) that is detectable, and preferably quantifiable, relative to established parameters of normality, is of relevance.

In addition, non-epithelial cells such as leukocytes are known to infiltrate cervical tissue as a consequence of pathological conditions. These may be enumerated by use of readily available monoclonal antibodies against pan-leukocytic markers, thus providing a further level of analysis.

Antibodies which are specific for a target of interest may be obtained using techniques which are standard in the art. Methods of producing antibodies include immunising a mammal (eg mouse, rat, rabbit, horse, goat, sheep or monkey) with the protein or a fragment thereof or a cell or virus which expresses the protein or fragment. Immunisation with DNA encoding the target polypeptide is also possible. Antibodies may be obtained from immunised animals using any of a variety of techniques known in the art, and screened, preferably using binding of antibody to antigen of interest. For instance, Western blotting techniques or immunoprecipitation may be used (Armitage et al, 1992, Nature 357: 80–82).

The production of monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. A hybridoma producing a monoclonal antibody may be subject to genetic mutation or other changes, which may or may not alter the binding specificity of antibodies produced.

As an alternative or supplement to immunising a mammal with a peptide, an antibody specific for a target may be obtained from a recombinantly produced library of expressed immunoglobulin variable domains, eg using lambda bacteriophage or filamentous bacteriophage which display functional immunoglobulin binding domains on their surfaces; for instance see WO92/01047. The library may be naive, that is constructed from sequences obtained from an organism which has not been immunised with the target or may be one constructed using sequences obtained from an organism which has been exposed to the antigen of interest (or a fragment thereof).

Antibodies may be modified in a number of ways. Indeed the term "antibody" should be construed as covering any specific binding substance having a binding domain with the required specificity. Thus this covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

It has been shown that the function of binding antigens can be performed by fragments of a whole antibody. Example binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, *Science*, 242, 423–426, 1988; Huston et al, *PNAS USA*, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444–6448, 1993).

Hybridomas able to produce monoclonal antibodies of use in the present invention have been deposited and represent individual aspects of the present invention, as do the monoclonal antibodies themselves. Thus, the present invention provides individually each of the hybridomas deposited as ECACC 95020718, 95020716, 95020720, 95020717 and 95020719, and mutants, derivatives and descendants of each of these hybridomas, whether or not able to produce antibody of the same or altered specificity.

The present invention also encompasses use of the hybridomas and antibodies obtainable therefrom in the obtention of other antibodies of use in the assessment of the state/condition of cervical cells in a tissue sample, ie able to bind to an antigen found on the surface of one or more cell types of the cervix. Such use may involve isolation of the antigen bound by any of the antibodies obtainable from the deposited hybridomas and use of the antigen in raising further antibodies, eg by immunisation and/or screening of 'phage libraries, as discussed above. The antigen may, for example, be isolated by immuno-precipitation from cervical cell extracts and then used as an immunogen eg for generation of further monoclonal antibodies, or in screening a 'phage library, as appropriate.

Additionally, nucleic acid encoding one of the antibodies may be isolated from any of the hybridomas and used in a recombinant expression system to produce whole antibody, an antibody fragment or chimaeras of antibody/antibody fragment fused to another polypeptide (eg label such as a peptide tag or enzyme). As mentioned above, cloning and expression of chimaeric antibodies are described in EP-A-0120694 and EP-A-0125023.

Recombinant expression of polypeptides, including antibodies and antibody fragments, is well-known in the art.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Transformation procedures depend on the host used, but are well known.

Thus, the present invention extends to any antibody or antibody fragment able to bind an antigen to which any (ie one or more) of the antibodies obtainable from the deposited hybridomas is able to bind. Ability to bind the same antigen may be assessed, for example in a binding inhibition assay or in a band-shift assay on an electrophoretic gel.

The present invention also provides in a further aspect the use of any antibody or antibody fragment of the invention, including those obtainable from any of the deposited hybridomas, in assessment of the nature or condition of cells of the cervix in a tissue sample, as disclosed.

Further aspects and embodiments of the present invention will be apparent to those skilled in the art.

Before illustrating embodiments of the present invention in more detail by way of example, it is helpful to understand the organisation of the cervix and the relationships between the different cell-types found there.

Cell Populations of the Cervix in Normal and Pathological Conditions

The cervix is essentially composed of two distinct cell types: the squamous epithelium and the columnar epithelium, each of which is located in an anatomically distinct region of the tissue. The squamous epithelium is located at the exterior aspect (the exocervix) of the cervical opening (the cervical os), while the columnar epithelium extends into the endocervical canal (the endocervix). These two distinct epithelial cell types come into contact in the vicinity of the cervical os, at the squamo-columnar junction. The squamo-columnar junction is of clinical importance as it is the region where the majority of malignancies arise. For diagnostic validity, a cervical smear sample must include cells from this region. In order to ensure that this has been achieved, a smear must contain columnar as well as squamous epithelial cells.

Columnar cells are the source of cervical mucous. They are generally arranged as a single cell layer lining the endocervix, which is thrown into deep folds to form the cervical glands. A small proportion (5%) of cervical tumours are derived from columnar cells i.e. the adenocarcinomas.

In some cervices, a cuboidal cell layer, the so-called reserve cell population, is disposed beneath the columnar cells. The role of reserve cells is unclear, but believed by many investigators to give rise to columnar epithelium.

In contrast to the columnar epithelium, the squamous epithelium, from which most (95%) cervical tumours arise, is a multilayered dynamic stem cell system under constant renewal.

The stem cell compartment itself is located adjacent to the basement membrane within the basal cell layer. Stem cell division gives rise to parabasal, intermediate, and superficial cell derivatives. These are conventionally defined in terms of both their characteristic morphology and location within the squamous epithelium. The transition from basal cells located in the deepest layer of the squamous epithelium, to superficial cells at its surface is associated with progressive differentiation and a loss of proliferation until superficial squamous epithelial cells at the cervical surface are terminally differentiated.

The transition zone (TZ), adjacent to the squamo-columnar-junction is of clinical importance, as it includes a region of metaplastic squamous-epithelium. This is generated at puberty, in response to the acidic environment of the vagina. The data presented herein quantify the proportion of samples where the TZ is present.

EXEMPLIFICATION OF EMBODIMENTS OF THE PRESENT INVENTION BY WAY OF ILLUSTRATION AND NOT LIMITATION

Abbreviations

ATCC—American Type Culture Collection; CIN—Cervical intra-epithelial neoplasia; CHAPS (3-[Cholamidopropyl)-dimethylammonio]-1-propanesulfonate); CD—Cluster Designation nomenclature of established cell markers; DAB—Di-amino benzidine; ECACC—European Collection of Animal Cell Cultures; EDTA—Ethylene di-amine tetra acetic acid; HLA—Human Leukocyte Antigen; HRPO—Horse radish peroxidase; Ig—Immunoglobulin; kDA—Kilo dalton; Mab(s)—Monoclonal antibody(ies); Mwt—Molecular weight; NS1—Non-secretor 1; PAGE—Polyacrylamide gel electrophoresis; PBS—Phosphate buffered saline; PAP—Papanicolau test; SDS—Sodium dodecyl sulphate; TBS—Tris buffered saline; TZ—Transition zone; W/V—Weight/volume ratio.

Cell Markers

The work disclosed herein shows that under normal conditions, cell surface markers may be gained or lost as cells within a given lineage proceed along their differentiation pathway. Therefore, monoclonal antibodies or other binding molecules exhibiting specific reactivities against these markers provide a means of monitoring the normal progression of cells along their differentiation pathway. In pathological conditions, the normal expansion or loss of these markers may be perturbed. Consequently, an expansion or loss of a cell surface marker is detectable as a particular cell population proliferates or becomes arrested at a discrete stage in its differentiation pathway.

The antibody reactivities described herein illustrate the situation where an overlapping continuum of reactivities is observed throughout normal squamous epithelial cell differentiation in the human cervix.

The designated nomenclature of the five monoclonal antibodies exemplified herein is:

1. CV3.6B5/F3/C2, hybridoma deposited as ECACC 95020718
2. 2C7/B4/D6., hybridoma deposited as ECACC 95020716
3. CV5.9G5.C6, hybridoma deposited as ECACC 95020720
4. HG3/E11/C4, hybridoma deposited as ECACC 95020717
5. BC4/E7/E5, hybridoma deposited as ECACC 95020719

Generally herein, these antibodies are referred to in their abbreviated forms. The hybridomas were deposited at European Collection of Animal Cell Cultures (ECACC), Centre for Applied Microbiology & Research, Salisbury, Wiltshire SP4 0JG, United Kingdom on Feb. 6, 1995.

Thus:

| | |
|---|---|
| Basal cells are | 6B5+ BC4– 9G5– HG3– 2C7– |
| Parabasal cells are | 6B5+ BC4+ 9G5– HG3– 2C7– |
| Intermediate cells are | 6B5– BC4+ 9G5+ HG3+ 2C7– |
| Superficial squames are | 6B5– BC4– 9G5+ HG3+ 2C7– |
| Columnar cells are | 6B5+ BC4– 9G5– HG3– 2C7+. |

These characteristic antibody reactivity profiles reproducibly define discrete stages in the differentiation of squamous epithelial cells. Additionally, they readily allow columnar epithelial cells to be distinguished from squamous epithelial cells.

Brief Description of Results

Immunoprecipitation of the 6B5 target protein from the cell surface of a cervical carcinoma cell line and from membrane preparations of cervical squamous epithelium:

(a) Cell surface proteins on the cervical carcinoma cell line C4II (Auersperg 1969. *J. Natl. Cancer Inst. USA* 43 151–173) were radioiodinated by the lactoperoxidase method (Marchalonis 1969. *Biochem J.* 113 299–305). Cells were solubilised with the detergent CHAPS (3-[3-Cholamidopropyl)-dimethylammonio]-1-propanesulfonate). Immunoprecipitations were carried out with test Mab against equal volumes of lysate (Houlihan et. al. 1992 *J. Immunol.* 149 668–675). The results show that Mab 6B5 detects a cell surface dimeric protein with components of approx. 181 and 184 kDa in a cervical epithelial cell line.

(b) Standard membrane extracts were prepared from sheets of cervical squamous epithelium (Evans 1979. Laboratory techniques in biochemistry and molecular biology, *Eds. Work and Work* 7 1–266, Elsevier). Membranes were radioiodinated using Iodobeads (Markwell 1982. *Anlyt. Biochem.* 125 427–432) and solubilised in CHAPS. Immunoprecipitations were carried out as described above. The results show that a similar form of this protein is also present in a membrane-associated fraction of cervical squamous epithelium shown in (a).

Immunoprecipitated material was analysed by SDS-PAGE under reducing conditions and autoradiography (Laemmli 1970. *Nature* 227 133–681).

Affinity Isolation of the 6B5 Target from C4II Cells

Affinity chromatography was performed as described by Houlihan et al. 1992 (*J. Immunol.* 149 668–675). Purified 6B5 antibody was conjugated to protein G-sepharose and cross-linked with dimethyl pimelimidate. $2 \times 10^8$ C4II cells were solubilised in the detergent CHAPS. The lysate was passed through a preclearing column containing mouse Ig-sepharose and protein A sepharose (Sigma) and then through the 6B5 antibody column. Both columns were washed with 10 bed volumes of lysis buffer and then eluted with 50 mM triethylamine, pH 11.5. The eluate was neutralised with 2 M glycine pH 2.0, concentrated by microultrafiltration and analysed by SDS-PAGE under reducing conditions and coomassie blue staining.

A single 180 kDa product was specifically isolated by the 6B5 column and detected in reduced eluates. This component was not observed in the eluate representing the negative control—mouse Ig/protein A sepharose column. Immunoglobulin H-chain which had leached during elution from the negative control column was present, however, in the mouse Ig/protein A sepharose eluate.

Immunoblotting of Detergent-Solubilised Endocervical Material using Antibody 2C7

Endocervical tissue was minced in Hanks buffered saline and proteins were solubilised in CHAPS (3-[3-Cholamidopropyl)-dimethylammonio]-1-propanesulfonate) buffer. The detergent soluble material was concentrated by microultrafiltration using a 30 kD cut-off filter. Proteins were electrophoretically separated on 1% agarose gels in Laemmli sample buffer under reducing conditions. Proteins were transferred to microporous membranes for immunoblotting. Identical strips were probed with Mab 2C7 and tissue culture supernatant as a negative control. Parallel strips were stained with periodic acid-Schiffs reagent which stains glycoproteins, and coomassie blue as a general protein stain (Methods were based on those of Morales et. al. 1993 *Human Reproduction* 8 78–83).-ve control immunoblot employed tissue culture supernatant.

Mab 2C7 specifically detects components migrating in the high m.wt. range that correspond to material stained by periodic acid-Schiff's reagent. The large m.wt (>500 kDa) of this material and detection by periodic acid-Schiff's reagent is consistent with the presence of mucins. The Mab showed no reactivity with any proteins in the significantly lower m.wt. material stained by coomassie blue.

Immunoblotting of Detergent-Solublised Cervical Epithelium using Mab 9G5

Squamous epithelial sheets were isolated from normal cervices using the enzyme Dispase (Boehringer). Sheets were solubilised in the detergent CHAPS (3-[3-Cholamidopropyl)-dimethylammonio]-1-propanesulfonate). Cytokeratin-enriched extracts were prepared from the CHAPS-insoluble material by the method of Franke et al. 1981 (*Exp. Cell Res.* 131 209–213). Both detergent (D) and cytokeratin (C) extracts were electrophoretically-separated by SDS-PAGE under reducing conditions (Laemmli 1970 *Nature* 227 133–681) and proteins were transferred to microporous membranes for immunoblotting (Towbin et al. 1979. *Proc. Natl. Acad Sci USA* 76 4350–4354).

Mab 9G5 detects a single 40 kDa product in detergent-solubilised extracts but not in cytokeratin extracts of cervical squamous epithelium. A pan-reactive cytokeratin Mab AH3 (J. M. Houlihan *Ph.D. thesis University of Bristol* 1993) was used as a control; keratins are detected in the cytokeratin extract.

Affinity Chromatographic Isolation of the 9G5 Target Protein from Human Amnion Cells Affinity chromatography was performed as described by Houlihan et al. 1992 (*J. Immunol.* 149 668–675). Purified Mab 9G5 was conjugated to protein G-sepharose and cross-linked with dimethyl pimelimidate. $2 \times 10^8$ amnion cells were isolated from the term placental membranes by incubation in trypsin followed by collagenase/hyaluronidase by the method of Holmes et al. 1990. (*J. Immunol.* 144 3099–3015) and solubilised in the detergent TX-100. The lysate was passed through preclearing columns, comprising mouse Ig and protein A sepharose and then the Mab 9G5 column. The Mab 9G5 column was eluted with 50 mM triethylamine, pH 11.5. The eluate was concentrated by microultrafiltration and analysed by SDS-PAGE under non-reducing conditions and coomassie blue staining.

A single 40 kDa product was isolated from amnion cell lysates by the Mab 9G5 affinity column. A fraction of this eluate was examined by immunoblotting with the 9G5 Mab and an irrelvant IgG1 Mab as a negative control. The 9G5 reacted with the 40 kDa product. The strip probed with the negative control Mab was blank.

Immunoblotting of Detergent-Solubilised Cervical Epithelium using Mab HG3

Squamous epithelial sheets were isolated from normal cervices using the enzyme Dispase (Boehringer). Sheets were solubilised in the detergent CHAPS (3-[3-Cholamidopropyl)-dimethylammonio]-1-propanesulfonate). Equal amounts of the CHAPS-soluble material were electrophoretically-separated by SDS-PAGE (Laemmli 1970. *Nature* 227 133–681) under both non-reducing and reducing conditions. Proteins were transferred to microporous membranes for immunoblotting (Towbin et al. 1979. *Proc. Natl. Acad Sci USA* 76 4350–4354). Parallel strips tested with Mab HG3; tissue culture supernatant was used as a negative control.

The negative control blot was blank.

(NR—non-reduced; R—Reduced)

Mab HG3 detects a product of approx. 180 kDa, under both non-reducing and reducing conditions, in detergent soluble cervical squamous epithelium.

Immunoblotting of Detergent-Soluble and Detergent-Insoluble Cervical Epithelium using Mab BC4

Squamous epithelial sheets were isolated from normal cervices using the enzyme Dispase (Boehringer). Sheets were solubilised in the detergent CHAPS (3-[3-Cholamidopropyl)-dimethylammonio]-1-propanesulfonate). CHAPS-soluble and CHAPS-insoluble material was adjusted to the same volume. Equal amounts of both soluble and insoluble fractions were electrophoretically-separated by SDS-PAGE (Laemmli 1970. *Nature* 227 133–681). The detergent soluble fraction was analysed under both non-reducing and reducing conditions while the detergent insoluble fraction was examined under reducing conditions. Proteins were transferred to microporous membranes for immunoblotting (Towbin et al. 1979. *Proc. Natl. Acad Sci USA* 76 4350–4354). Parallel strips were tested with Mab BC4; tissue culture supernatant was used as a negative control.

The negative control blot was blank.

Mab BC4 detects a protein of 200–210 kDa in non-reduced, but not in reduced, detergent soluble extracts of cervical squamous epithelium. No product was detected in detergent insoluble fraction of cervical squamous epithelium.

Cervical Biopsies

Most of the data herein has been obtained from extensive investigations undertaken on biopsy material, for the following reasons:

(a) A single biopsy specimen provides several serial tissue sections (each 5 um thick) for microscopic examination. All sections are therefore almost identical, and the various cell populations located in the same positions relative to each other. Similarity in anatomical structure, at the cellular level, is therefore maintained between samples.

This enables reactivities of different antibodies to be investigated and compared, on the same cell populations, between samples.

Different cell populations within a tissue are identified by their individual morphologies and locations. Therefore, the reactivities of individual antibodies against such cells in a biopsy sample, enables their specificities to be determined and established.

(b) Pathological changes are accompanied by a disruption of the normal histology of the tissue. Therefore, antibody reactivities can only be effectively investigated (and correlated with pathological conditions) in samples, where the tissue architecture is representative of the situation in vivo.

Pathological changes that precede malignancy are classified according to an established system of grading: CIN I, II and III. The progression of disease leads to carcinoma in situ and finally a frank tumour.

(c) Most importantly, the use of biopsy material was necessary to determine whether modulation of expression of the antibody targets occurred as a function of disease in the cervix. The profiles of antibody reactivities on tissue sections of normal biopsies provided a framework to establish their corresponding reactivities on abnormal smears. Such reactivities on normal and abnormal biopsies enabled the selection of antibodies for use in a cervical smear screening system, in accordance with the present invention.

Cervical Smears

The cells in a smear sample do not maintain their topographical relationships to each other, as in a tissue section of a biopsy. Antibodies selected on the basis of their specificities against various cell populations (as above), were investigated for their ability to provide qualitative or quantitative information on normal and pathological smear samples. Their absolute or relative numbers, enumerated with these antibodies, provides a means of determining detectable changes in these cell populations.

Tissue Distribution

Although the monoclonal antibodies were raised against cervical epithelium, they would be expected to react against their target epitopes if present on non-cervical epithelium of shared embryological origin. Therefore, their tissue distribution in other epithelial tissue was determined, enabling further characterisation at that level.

Biochemical Data

These have been mainly derived using extracts of cervical amnion and placental tissue, electrophoretically separated on SDS-PAGE gels under reducing or non-reducing conditions. Western blots of the resolved components were then probed with the panel of monoclonal antibodies, enabling their individual target epitopes to be defined at the molecular level.

The detection of such resolved components under defined experimental conditions provides information on the molecular structure of the target antigen. If detected under both reducing and non-reducing conditions, it can be deduced to be a non-conformationally dependent monomeric structure. On the other hand, if only detected under non-reducing conditions, the epitope is present on a conformationally dependent structure.

The methods of extraction enable the identified material to be assigned to known classes of cell markers. For example, use of detergents do not provide extracts with appreciable amounts of cytokeratins. The cytokeratins are a complex family of cytoplasmic filamentous protein structures that are well documented in the scientific literature. They are biochemically and antigenically related to varying degrees, and are expressed in different epithelia in different combinations of polypeptides. A given epithelium or epithelial cell can therefore be characterized by the specific pattern of its cytokeratin components [Ref: Moll R et al, 1982].

Furthermore, with the exception of Mab 9G5, the molecular weights of the target antigens precluded them from belonging to the cytokeratin family. A monoclonal antibody (AH3) with pan-Cytokeratin reactivity was used to confirm that the 9G5 epitope was a non-cytokeratin cell marker. This antibody has been previously described [Ref: Houlihan 1993].

Where sufficient or suitable biopsy material was not obtainable, established carcinoma cell lines derived from cervical tissue were utilised to prepare such extracts.

Trypsin Sensitivity

The susceptibility of target epitopes to proteolysis by trypsin was determined. The enzyme's pronounced substrate specificity (restricted to lysine and arginine residues) provides a means of characterising the target epitopes further.

Materials and Methods

Standard buffers and reagents were prepared in accordance with established procedures that are well documented in the scientific literature so need not be detailed here. Unless otherwise stated, all chemicals were obtained from Sigma Chemical Co, Poole, Dorset, UK.

Preparation of Immunogen and Immunisation

Three sources of cervical cells: (A) smear samples, (B) hysterectomies and (C) premalignant CIN biopsies were evaluated for their potential use as immunogen:

(A)

Cervical smears from routine samples were dispensed into sterile PBS and washed twice. The yield, composition and viability of cells in smears taken from different sites within the cervix was examined. The cellular composition of conventional smears taken from the exocervix using a spatula, was compared with endocervical smears taken with a brush. Yields of squamous cells in exocervical smears varied; obtaining up to $10^6$, with viabilities of 50–60%. Endocervical smears gave much lower yields of typically $10^4$, which also contained predominantly squamous cells.

Cytospin preparations of cervical smear samples were also examined immunohistologically and identified using anti-cytokeratin antibodies. The overwhelming majority were squames; the preparations contained few basal, parabasal, or columnar epithelial cells. It was concluded that cervical smears did not represent an effective source of material for use as immunogen, since they did not contain a sufficient cross section of cervical epithelial cell populations.

(B)

Total hysterectomy specimens are typically obtained from women with menorrhagia or fibroids; in these, the cervix is essentially normal. Such specimens are typically in the perimenopausal (38–45 yr old) period. The optimal method for obtaining single cell suspensions from whole normal cervical biopsy material was determined to be as follows.

The excess stromal tissue was removed with a scalpel. The fragments of tissue were floated in a solution of the enzyme Dispase II (1.2 units/ml, Boehringer Mannheim, Sussex, UK) in HANKS buffered saline lacking $Ca^{2+}/Mg^{2+}$ overnight at 4° C. This procedure disrupted the epithelial/stromal junction, such that sheets of epithelial cells could be gently teased apart. They were washed by low speed centrifugation in HANKS buffered saline lacking $Ca^{2+}/Mg^{2+}$ and resuspended in 0.05% trypsin/0.02% EDTA (both w/v). After a 30 minute incubation at 37° C. with stirring, trypsinization was arrested by the addition of 1.3 mg (in 5 ml of saline) of soya bean trypsin inhibitor.

The secondary enzyme digestion with trypsin disaggregated the epithelial sheets to generate a single cell suspension.

Large fragments were allowed to settle out under gravity and the supernatant was removed. The cell suspension was drawn through a 16 gauge needle to break up cell clumps, and filtered through a 100 um gauze. Cells were washed twice in PBS prior to use as immunogen.

(C)

In addition to normal cervical biopsies, immunogen from pathological CIN II/III biopsies were also used. The material was treated similarly, except for the initial overnight enzyme treatment also being in trypsin.

The immunisation regime consisted of an initial intraperitoneal inoculation of $5 \times 10^5$ cells as a priming dose, followed by five further immunisations of $0.5–2 \times 10^6$ normal epithelial cells, at 2–3 weekly intervals in 8 week old female Balb/c mice.

As some proteolytic cleavage of cell surface components was possible, the effect of enzyme treatment on the integrity of epithelial cell surface markers was ascertained. This was determined by monitoring its effect on CD44, CD55 and HLA Class 1 antigens, all of which are expressed on cervical epithelial cells. These established cell surface markers can be detected by appropriate monoclonal antibodies which are readily commercially available [Ref: Knapp W, 1989]. These markers were found to be lost or reduced as a consequence of prolonged exposure to trypsin at 37° C. However, adopting measures to minimise such effects i.e. reduced exposure at 37° C. and use of the enzyme dispase in the initial overnight incubation at 4° C. instead, ensured that the phenotypic profile of the disaggregated cells was maintained very closely to that of native cervical epithelium.

Fusion and Assay of Supernatants from Hybridomas

Splenocytes from the immunised mice were fused with NS1 murine myeloma cells, and hybrids selected by conventional methodology that is described in a number of publications [Ref: Kennet R et al, 1980, and Schrier M et al, 1980].

Candidate monoclonal antibodies were selected on the basis of their reactivities on tissue sections of cervical biopsies using established immunohistological techniques [Ref: Holmes C H et al, 1990].

Briefly, sections were cut from frozen tissue blocks in a cryostat at 5 µm thickness, thawed, air dried at room temperature for 1 hour, fixed in ice-cold acetone for 10 mins and immunostained by an indirect immunoperoxidase technique. Supernatants, from wells containing growing hybridomas, were incubated for 45 mins at room temperature on tissue sections. After washing in TBS for 5 minutes, they were incubated for 30 mins with a commercially available HRPO-conjugated rabbit anti-mouse Ig reagent, optimally diluted in TBS containing 10% normal human serum. After two more washes, sections were developed with DAB and hydrogen peroxide for 5 mins. After stopping the reaction by washing the slides in tap water for 5 mins, the sections were counterstained in haematoxylin, dehydrated, cleared in Histoclear and mounted in DPX mountant.

Candidate hybridomas, secreting antibodies of interest, were cloned to stability by the method of limiting dilution. The antibodies secreted by such clones were reassayed to confirm antibody specificity by immunostaining, as above.

Ig production by hybridomas was also screened by an ELISA technique, using commercially available reagents from Dako AS, Copenhagen, Denmark): Rabbit anti-mouse Ig (product no: Z259) optimally diluted at 1/2000 was used as the solid phase capture reagent. Supernatants from hybridomas were incubated for 60 min; bound antibody was detected with a HRPO-conjugated rabbit anti-mouse Ig (product no: P260) diluted 1/1000 incubated for 45 mins. Both incubations were at room temperature; the reagents were diluted in PBS, and the wells washed between incubations with PBS-0.025% Tween.

Biochemical Characterisation

The methods utilised are generally well known and documented in published laboratory technical manuals [Ref: Harlow E and Lane D, 1988 and Work and Work, 1979] and in individual publications [Ref: Marchalonis, 1969; Markwell, 1982; and Laemmli, 1970]. Detailed descriptions of specific procedures undertaken in these investigations have been previously published [Ref: Holmes C H et al 1990 and Houlihan J M et al, 1992].

EXAMPLE 1

Mab 6B5

This antibody of isotype IgG1 was raised against an immunogen prepared from squamous epithelial cells isolated from the cervices of hysterectomy specimens.

Reactivity

Its specificity is mainly against parabasal and basal cells in cervical squamous epithelium together with basement membrane. However, it also cross-reacts with columnar epithelium and non-epithelial stromal elements.

Although parabasal cells are not present in large numbers in normal smears, the antibody does identify the small number that are present; based cells are usually not present in smear samples. However, 6E5 reactivity increases significantly in pathological conditions. With tumours, 6/7 squamous cell carcinomas showed antibody reactivity. This reactivity was retained on one adenocarcinoma; this was expected, as 6B5 also reacts with normal columnar cells. There is also an expansion of 6B5 reactivity in CINs: in 9/15 moderate to severe CIN specimens tested, there was a marked expansion in the affected squamous epithelium relative to the native unaffected epithelium.

The anti-stromal reactivity is only of relevance in biopsy material, as stromal elements are not present in smear samples. The anti-columnar reactivity is not expected to interfere in the intended mode of application, as adequate controls exist to correct for this effect (see reactivity of Mab 2C7).

(a) Normal Cervical Epithelium

No of tests: 90; No of patients: 44 (with TZ: 21)

Parabasal cells and basement membranes were intensely reactive in squamous epithelium. Columnar cells were also positive, with reactivity expanded in the transformation zone in 21/21 specimens.

(b) Premalignant Cervical Epithelium (CIN II/III or III)

No of tests: 42; No of patients: 30 (with CIN: 15)

The reactivity was expanded in 9/15 CIN specimens.

(c) Cervical Carcinomas

The antibody reacted strongly with 5/7 squamous cell carcinomas and with both adenocarcinomas tested.

Tissue Distribution

Despite its restricted distribution in the cervix, the target epitope is present in other epithelial tissue:

Placenta

Epithelial cells in term placental membranes (amnion and cytotrophoblasts) are positive. The basement membrane beneath the syncytiotrophoblast is positive. In first trimester placenta, both villous cytotrophoblast and syncytiotrophoblast are positive. The antibody shows differential activity with cytotrophoblast in extravillous cell columns: cells at the base of these columns are positive while those at the periphery are negative.

| | |
|---|---|
| Kidney: | glomeruli +; tubules − |
| Pancreas: | ducts and acini +; lamina propria − |
| Colon: | epithelium +; lamina propria − |
| Liver: | hepatocytes +; bile duct/mesenchymal cells − |
| Endometrium: | glandular epithelium −; lamina propria −; myometrium −; arteries − |
| Epidermis: (foreskin) | parabasal cells +; basement membrane + basal cells +/−; intermediate cells −; superficial cells − |

Biochemical

Because of its limited reactivity in the normal cervix, an established cervical carcinoma cell line C4II was used to characterise this antibody biochemically. The C4II cell line [Ref: Auersperg N and Hauvryl AP, 1962 and Auersperg N, 1969] obtained from ECACC, Porton Down, UK is well documented in the scientific literature. It is also deposited in the ATCC under Accession No. CRL 1595.

Mab 6B5 detects a dimeric product of approximately 181–184 kDa, by immunoprecipitation on the cell surface of C4II. A single component having this molecular weight has subsequently been immunoprecipitated directly from radio-labelled membrane preparations of normal in vivo-derived cervical squamous epithelial cells. However, the antibody does not detect these components on cervical extracts by western blotting. Taken together, these data indicate that Mab 6B5 detects a conformationally-dependent epitope on a cell surface (non-cytokeratin) protein. The 6B5 target has also been isolated to a high degree of purity by immunoaffinity chromatography, for N-terminal sequencing.

Trypsin Sensitivity

The reactivity of the antibody is maintained with the C4II cell line after a short 10 min exposure to trypsin at 0.05% (w/v). However, antibody reactivity with placental membranes or amnion cells is abolished after a longer 1 hr exposure to trypsin at 0.1% (w/v). The antibody target is therefore only partially resistant to trypsin.

EXAMPLE 2

Mab 2C7

This antibody of isotype IgG1 was raised against an immunogen prepared from normal cervices of hysterectomy specimens.

Reactivity

The antibody reacts specifically and solely with columnar epithelial cells.

(a) Normal Cervical Epithelium

No of tests: 83; No of patients: 43 (with TZ: 24)

This antibody reacted specifically with columnar epithelial cells, and not with any other cell population in the cervix. The squamous epithelium was negative in all cases.

(b) Premalignant Cervical Epithelium (CIN II/III or III)

No of tests: 42; No of patients: 30 (with CIN: 15)

No reactivity with either normal or neoplastic epithelium; only adjacent columnar epithelium was stained.

(c) Cervical Carcinomas

The antibody did not react with 7/7 squamous carcinomas tested, as expected. However, it reacted with one of the two adenocarcinomas tested.

It can be concluded that the target epitope of Mab 2C7 is solely restricted to columnar cells, and not expressed in either normal squamous epithelium or in CIN lesions. The antibody is considered useful since the presence of columnar cells on a smear indicates that the squamo-columnar junction has been sampled, and hence that the smear is patent (or adequate). A correctly sampled smear therefore contains between 1–5% of 2C7 reactive cells.

The 2C7 target epitope is distinct from that of 6B5. In normal smears, both antibodies identify the columnar cell population. However, whilst 6B5 additionally reacts with parabasal cells, 2C7 only detects columnar cells. Therefore, together, they provide a means of enumerating both cell populations by analysis of their individual reactivity profiles.

| Tissue Distribution | |
| --- | --- |
| Placenta: | The amnion and cytotrophoblast in placental membranes, and syncytiotrophoblast were negative in first trimester placentae and at term. |
| Pancreas: | Epithelium of ducts + |
| Colon: | Glandular epithelium + |
| Tonsil: | Stratified epithelium − |
| Epidermis: | Foreskin − |
| Liver: | Hepatocytes− ; bile duct +/− |
| Endometrium: | Epithelium − |

Biochemical

Detergent extracts of endocervical epithelium were prepared by incubating fragments of endocervix in buffer containing CHAPS. On Western blots of material separated by SDS-PAGE, the antibody reacted with unresolved high Mwt components of >400,000 kDA in these extracts. This was further investigated by resolving the extracted material on 1% agarose gels, which are more suitable than SDS-PAGE gels for larger molecules. The antibody reacted with components that precisely corresponded to a fraction that also stained with periodic acid-Schiff's base, but not with Coomassie Blue. This indicated that the target epitope represented a mucin or a mucin-associated product.

Trypsin Sensitivity

The target epitope appears to be trypsin insensitive, as the antibody reacted with cell preparations of cervical tissue which had been trypsinised for periods of up to 1 hr.

EXAMPLE 3

Mabs 9G5 and HG3

Both antibodies are of isotype IgG1.

Mab 9G5 was raised against an immunogen prepared from squamous epithelial cells isolated from normal cervices of hysterectomy specimens.

Mab HG3 was raised against an immunogen prepared from cervical biopsies of pathological CIN material.

Reactivity

Both antibodies react primarily with superficial and intermediate squamous epithelium in the cervix.

(a) Normal Cervical Epithelium

No of tests: 83; No of patients: 44 (with TZ: 21 for Mab 9G5 and 24 for Mab HG3)

Both antibodies have similar patterns of reactivity in the normal cervix, with specificities against superficial and intermediate squamous epithelial cells. They are unreactive with basal cells; however, Mab 9G5 reacts with parabasal cells in some specimens, where the reactivity fades within the upper parabasal layer. In contrast, Mab HG3 does not react with parabasal cells in any of the specimens.

Mab 9G5 does not react with columnar cells; however, Mab HG3 shows weak reactivity on columnar cells in a small number of specimens.

(b) Premalignant Cervical Epithelium (CIN II/III or III)

No of tests: 42; No of patients: 30 (with CIN: 15)

In general, both antibodies show detectable differences between normal and abnormal cervical epithelium. The reactivity is modulated in CINs, where it is either reduced or absent; e.g. the reactivity of Mab 9G5 is markedly reduced in 10/15 specimens. In these lesions, the depth of immunostaining (denoting antibody reactivity) is reduced in terms of the number of cell layers, when compared to normal squamous epithelium.

(c) Cervical Carcinomas

Both antibodies differed in their reactivities against the seven squamous cell carcinomas tested:

Mab 9G5 was completely unreactive with 3/7 specimens tested. The remaining 4 tumours showed heterogenous reactivity.

Mab HG3 showed extensive reactivity with 3/7 of the squamous cell carcinomas, some reactivity with 2, and was unreactive with the remaining 2.

Heterogeneity is defined as areas of both reactivity and unreactivity within a particular specimen. Generally, despite similar reactivities in the normal cervix, the reactivity of Mab 9G5 with these tumours was more limited than that of Mab HG3. In particular, Mab 9G5 was negative with two tumours which Mab HG3 reacted extensively with.

When tested on two adenocarcinomas, Mab HG3 reacted with both tumours; whereas Mab 9G5 was unreactive against both.

Mabs 9G5 and HG3 recognise distinct target epitopes on the same cell populations. However, it is considered desirable to utilise them in tandem, for the following reasons:

(a) It is not known whether all cells that comprise the intermediate and superficial cell population display both target epitopes. Even if they normally do, their expression may modulate with stages of the cell or oestrus cycles.

(b) As superficial epithelial cells are a mainly dead or dying cell population, it is conceivable that their surface markers would be heterogenous in their detectability.

(c) Cervical smears are largely comprised of superficial and intermediate cells; with columnar and parabasal cells being a minority. Consequently, a decisive factor in deriving conclusions regarding the clinical status of the sample, would be based on the information concerning these cells.

For these reasons, it may be prudent to avoid dependence on a single antibody. Therefore, both antibodies may be utilised to enumerate or analyse absolute or relative numbers of intermediate and superficial squamous cells in normal or pathological conditions.

| Tissue Distribution | |
| --- | --- |
| Kidney, pancreas: liver and endometrium | Negative |
| Colon: | Mab 9G5 − ; Mab HG3 + |
| Tonsil: | Stratified epithelium + |
| Epidermis (foreskin): | Superficial and intermediate cells + |
| Placenta : | Amnion and cytotrophoblast in placental; membranes + Synciotrophoblast + |

[In the first trimester, these trophoblast populations were either negative or only weakly stained.]

Biochemical

Mab 9G5 cross-reacts with amnion and placental trophoblast epithelium. On immunoblots, it detects a prominent 40 KDa component under both reducing and non-reducing conditions, from detergent extracted material. Therefore, the 9G5 target epitope is likely to be on a non-cytokeratin monomeric protein, which is not conformation dependent. Micro-sequence analysis indicates that the N-terminus is blocked by a methionine residue; further sequence analysis is in progress on proteolytic digests of the intact molecule. Mab HG3 detects a 180 KDa component under reducing and non-reducing conditions, in both detergent soluble and membrane preparations of both amnion and cervix. Therefore, its target epitope is also likely to be a conformationally independent monomeric protein.

EXAMPLE 4

Mab BC4

This antibody of isotype IgM, was raised against epithelial cells isolated from premalignant cervical biopsies containing CIN.

Reactivity

The antibody primarily reacts with parabasal and intermediate cells in the cervix.

(a) Normal Cervical Epithelium

No of tests: 85; No of patients: 44 (with TZ: 24) Typically, the reactivity encompasses 2–6 cell layers above the parabasal layer, and therefore can include the lower layers of intermediate squamous cells. Basal cells, superficial squames and columnar cells are negative.

This reactivity pattern, when compared with that of Mabs 6B5, 9G5 and HG3 (see Table 1), enables the intermediate squamous cell population to be enumerated by appropriate deduction.

(b) Premalignant Cervical Epithelium (CIN II/III or III)

No of tests: 42; No of patients: 30 (with CIN: 15)

Reactivity on parabasal cells in CIN specimens is either absent or grossly disrupted in 7/15 specimens. Where there was a complete loss of reactivity, the loss occurred abruptly at the junction between normal and premalignant tissue. Where the reactivity was reduced, it was in terms of the number of immuno-stained cell layers.

(c) Cervical Carcinoma

The antibody reacted with 2/7 squamous cell carcinomas tested; of these one was heterogenous in its reactivity.

The two adenocarcinomas were unreactive.

Tissue Distribution

| Placenta: | All placental tissue, both first trimester and term are negative. |
|---|---|
| Kidney: | Negative |
| Pancreas: | Negative |
| Colon: | Negative |
| Liver: | Negative |
| Endometrium: | Negative |
| Buccal cavity: | Parabasal cells and stratified epithelium associated with tonsils are positive. |
| Epidermis: (foreskin) | Parabasal cells are positive. |

Biochemical

The target epitope was probed on immunoblots from detergent-solublised extracts and membrane preparations of enzyme disaggregated cervical epithelial tissue. The antibody detected a 200 KDa structure under non-reducing conditions only. The target epitope is therefore likely to be present on a conformationally-dependent, non-cytokeratin, protein.

EXAMPLE 5

Assessment of Cervical Cells; Comparison with PAP Test

The work described in the preceding examples has resulted in the generation of a panel of antibodies with reactivities against epithelial cell populations of the human cervix. The reactivities generally overlap, with the exception of Mab 2C7 which reacts specifically with columnar cells. The overlapping specificities of the other four antibodies (6B5, BC4, 9G5 and HG3) demonstrate a continuum of reactivities that parallel the differentiation lineage of cervical squamous epithelial cells themselves. It is most probable that the antibody target epitopes are normal differentiation markers which are expressed and lost as the cells differentiate from basal to terminal superficial squames.

The data herein suggests a scenario wherein with the onset of premalignant (CIN) or neoplastic disease conditions, cells can become arrested at a particular stage of differentiation. This may result in an expansion of a particular cell population expressing a detectable cell marker. For example, the anti-parabasal cell reactivity of Mab 6B5 is expanded in specimens with severe CIN II/III.

Similarly, a pathological condition may result in an expanded cell population accompanied by the concomitant loss of a characteristic cell marker. For example, the reactivity of Mab BC4, which also reacts against parabasal cells in normal epithelium, is reduced in CIN samples.

The reactivities of Mabs 9G5 and HG3 against intermediate and superficial squames is markedly reduced in premalignant CIN samples. This could be due to a reduction in the absolute number of intermediate and superficial squames, as a consequence of arrested differentiation at the parabasal stage. Conversely, it could be due to a loss of the relevant cell markers themselves, as a result of the pathological condition.

It should be noted that an actual expansion or reduction in the absolute numbers of a particular cell population is not a pre-requisite for the purposes of the present invention. Any detectable change in antibody binding relative to established parameters of normality is relevant and of use in the present invention. No particular theory or hypothesis limits the nature and scope of the present invention.

A data bank of numerical parameters pertaining to normal smears establishes the "confines of normality", against which test samples may be compared. Any significant variance from the established parameters indicates a need for individual diagnosis by suitably qualified personnel, to assess the clinical status, ie suspect samples are highlighted using the present invention for further examination.

Experimental Results

Reactivity of the antibodies 9G5, HG3, 6B5, BC4 and 2C7 was assessed on normal cervical smear samples and CIN-2/CIN-3 cervical smear samples, which were also analysed by the PAP test. The results are shown in Tables 3 and 4.

Normal cervical smear material was collected in parallel with pathological smear samples in a colposcopy clinic. Following the deposition of the primary smear on a glass slide for Papanicolaou staining, the sampling device, either spatula or brush, was placed in 10 mls of Hanks buffered saline and agitated. Samples showing obvious contamination with blood were discarded. The resulting cell suspensions were then washed x2 in this buffer and used to generate cytospins.

Each cytospin spot contained approximately $10^4$ cells.

The MAb reactivities were detected by an indirect immunostaining technique using a Streptavidin-Biotin, alkaline phosphatase detection system. The chromogen (Fuschin; Dakopatts) produced a red stain. Cell nuclei were counterstained with Mayer's haematoxylin.

Scoring of % cells stained was determined by counting dispersed cells; total cells stained red/total no. nuclei. Cell clumps are often present in such preparations and the reactivity of the Mab with these is indicated separately.

The status of the smear sample, normal or CIN, is given as designated by cytological examination (PAP) of the parallel specimen.

Table 3 shows that a pattern of normality for binding of the five monoclonal antibodies can be perceived. In the CIN samples binding of the same antibodies deviates from this pattern of normality, as shown in Table 4.

It should be noted that in the case of specimens 6 and 7, visually these samples appeared similar to normal smears. On morphological grounds, the majority of cells were obviously superficial squames and dyskaryotic cells were not apparent. In other specimens, for example, 1, 2, 3 and 10, dyskaryotic cells were clearly evident.

Thus, one can establish a pattern of normality for binding of a panel of antibodies to a sample containing cells of the cervix such that deviation from that pattern in binding of those antibodies to a test sample is indicative of some abnormality which warrants further investigation.

All documents mentioned herein are incorporated by reference.

REFERENCES

Auersperg N and Hauvryl A P, J Nat Cancer Inst 28: pp 605–627, 1962.
Auersperg N, J Nat Cancer Inst 43: pp 151–173, 1969.
Harlow E and Lane D (Eds), Antibodies: A Laboratory Manual, Cold Spring Harbor Laboratory, 1988.
Holmes C H et al, J Immunology 144:, pp 3099–3105, 1990.
Houlihan et al, J Immunology 149: pp 668–675, 1992.
Houlihan J M, PhD Thesis, University of Bristol, 1993.
Kennet R et al (Eds), Monoclonal Antibodies and T-Cell Hybridomas (Plenum Press, 1980).
Knapp W (Ed), Leukocyte Typing IV, Academic Press, London, 1989.
Laemmli U K, Nature 227: pp 133–681.
Marchalonis J J, Biochem J. 113: pp 299–305.
Markwell, Analyt. Biochem. 125; pp 427–432.
Schrier M et al, Hybridoma Techniques, Cold Spring Harbour Laboratory, 1080.
Work and Work (Eds), Laboratory Techniques in Biochemistry and Molecular Biology, Elsevier, 1979.

TABLE 1

SUMMARY OF MONOCLONAL ANTIBODY REACTIVITIES AGAINST NORMAL CERVICAL EPITHELIAL CELLS IN BIOPSY PROVEN NORMAL CERVICES.

| Target Cell Populations | Monoclonal Antibodies | | | | |
|---|---|---|---|---|---|
| | 2C7 | 6B5 | BC4 | 9G5 | HG3 |
| Basal | − | +/− | − | − | − |
| Parabasal | − | + | + | +/− | − |
| Intermediate Squames | − | − | +/− | + | + |
| Superficial Squames | − | − | − | + | + |
| Columnar | + | + | − | − | − |

TABLE 2

REACTIVITY OF MABS 9G3 AND HG3 ON CERVICAL CARCINOMAS

| Tumour | Type | 2C7 | 6B5 | BC4 | 9G5 | HG3 |
|---|---|---|---|---|---|---|
| A | Squamous | − | +++ | − | +/− | − |
| B | Squamous | − | − | − | − | +++ |
| C | Squamous | − | +++ | − | +/− | +++ |
| D | Squamous | − | + | − | − | − |
| E | Squamous | − | + | +/− | +/− | +/− |
| F | Squamous | − | +/− | − | − | +++ |
| G | Squamous | − | − | +/− | +/− | +/− |
| H | Adenoc. | +++ | + | − | − | +++ |
| I | Adenoc. | − | + | − | − | + |

Squamous = Squamous Cell Carcinoma
Adenoc. = Adenocarcinoma
+/− Heterogenous reactivity defined as areas of both reactivity and unreactivity within a specimen.
+ Positive Reactivity.
+++ Extensive intense reactivity.

TABLE 3

REACTIVITY OF MONOCLONAL ANTIBODIES WITH NORMAL CERVICAL SMEARS.

| | (Squamous) | | (Parabasal) | | (Columnar) |
|---|---|---|---|---|---|
| Specimen | 9G5[1] | HG3[1] | 6B5[2] | BC4[2] | 2C7[2] |
| 1. | 75% | 88% | −ve | −ve | −ve |
| 2. | 68% | 86% | −ve | −ve | −ve |
| 3. | 65% | 70% | −ve | −ve | >50 |
| 4. | 75% | 85% | −ve | −ve | −ve |
| 5. | 62% | 79% | −ve | −ve | −ve |
| 6. | 93% | 68% | 5 | 1 | −ve |
| 7. | 83% | 74% | 2 | −ve | >100 |
| 8. | 72% | 85% | 7 | 3 | +ve[$] |
| 9. | 68% | 90% | −ve | −ve | 10 |
| 10. | 85% | 90% | −ve | −ve | −ve |
| mean | 74.6 ± 9.79 | 81.5 ± 8.22 | | | |

Footnotes
[1]200 cells were counted in the case of 9G5 and HG3.
[2]Numbers given refer to positive cells in the whole field containing approx. 10[4] cells.
[$]Clumps of stained cells were observed.

TABLE 4

REACTIVITY OF MONOCLONAL ANTIBODIES WITH CERVICAL SMEARS FROM PRE-MALIGNANT SPECIMENS WITH CIN-2/CIN-3

| | | (Squamous) | | (Parabasal) | | (Columnar) |
|---|---|---|---|---|---|---|
| Patient | Grade | 9G5[1] | HG3[1] | 6B5[2] | BC4[2] | 2C7[2] |
| 1. | CIN-3 | <5% | <2% | −ve | −ve | +ve[$] |
| 2. | CIN-3 | NT | <5% | −ve | −ve | +ve[$] |
| 3. | CIN-3 | <20% | ND | >50[$] | ve | 10[$] |
| 4. | CIN-3 | 60% | 20% | −ve | −ve | 1 |
| 5. | CIN-3 | 50% | 96% | −ve | −ve | −ve |
| 6. | CIN-3 | 75% | 73% | 10 | 5 | −ve |
| 7. | CIN-3 | 86% | 78% | ve | −ve | 10 |
| 8. | CIN-2/3 | 54% | <10% | >20 | 2[$] | −ve |
| 9. | CIN-2/3 | 59% | 52% | ve | −ve | 20 |
| 10. | CIN-2 | 15% | 15% | 19 | −ve | 4% |
| 11. | CIN-2 | 38%[$] | 20% | vs | −ve | 1 |

Footnotes
[1]200 cells were counted in the case of 9G5 and HG3.
[2]Numbers given refer to positive cells in the whole field containing approx. 10[4] cells.
[$]Clumps of stained cells were observed.

What is claimed is:

1. A method of screening for a premalignant or neoplastic disease state in the squamous cells of a cervical smear sample containing columnar and squamous cells of the cervix, the method comprising contacting said sample with a panel of two or more monoclonal antibodies, said panel of antibodies including at least one monoclonal antibody specific for columnar cells and at least one monoclonal antibody specific for squamous cells, wherein said panel of monoclonal antibodies binds to surface antigens of normal columnar and squamous cells;

verifying that the cervical sample comprises columnar cells by detecting the binding of the monoclonal antibody specific for columnar cells in the cervical sample;

comparing the pattern of binding of the panel of monoclonal antibodies in said sample with the pattern of binding of said monoclonal antibody panel to a normal cervical cell sample, wherein an alteration of the pattern of binding of the monoclonal antibody or antibodies which bind to squamous cells in the cervical smear sample relative to the pattern of binding of the monoclonal antibody or antibodies which bind to squamous cells in a normal cervical cell sample is indicative of a premalignant or neoplastic disease state.

2. A method of screening for a premalignant or neoplastic disease state in the squamous cells of a cervical smear sample containing columnar and squamous cells of the cervix, the method comprising contacting said sample with a panel of two or more monoclonal antibodies, said panel of antibodies including at least one monoclonal antibody specific for columnar cells and at least one monoclonal antibody specific for squamous cells, wherein said panel of monoclonal antibodies binds to surface antigens of normal columnar and squamous cells;

verifying that the cervical sample comprises columnar cells by detecting the binding of the monoclonal antibody specific for columnar cells in the cervical sample;

comparing the pattern of binding of the monoclonal antibody or antibodies which bind to squamous cells in the cervical smear sample with the pattern of binding of said monoclonal antibody or antibodies which bind to squamous cells in a normal cervical cell sample, wherein an alteration of the pattern of binding is indicative of a premalignant or neoplastic disease state and wherein the panel includes one or more monoclonal antibodies comprising an antigen binding domain obtainable from a hybridoma selected from those deposited at the European Collection of Animal Cell Cultures (ECACC), under the accession numbers ECACC 95020718, ECACC 95020716, ECACC 95020720, ECACC 95020717 and ECACC 95020719.

3. A method according to claim 1 wherein one or more of the monoclonal antibodies bind to an antigen which can be bound by one or more antibodies obtained from a hybridoma selected from those deposited at the European Collection of Animal Cell Cultures (ECACC), under the accession numbers ECACC 95020718: ECACC 95020716: ECACC 95020720, ECACC 95020717 and ECACC 95020719.

4. A hybridoma selected from those deposited at the European Collection of Animal Cell Cultures (ECACC), under the accession numbers ECACC 95020718, ECACC 95020716, ECACC 95020720, ECACC 95020717 and ECACC 95020719.

5. A monoclonal antibody which specifically binds to the surface or normal squamous or columnar cells or the cervix comprising an antigen binding domain obtainable from a hybridoma selected from those deposited at the European Collection of Animal Cell Cultures (ECACC), under the accession numbers ECACC 95020718, ECACC 95020716, ECACC 95020720, ECACC 95020717 and ECACC 95020719.

6. The method as claimed in claim 1 wherein said panel of monoclonal antibodies comprises a monoclonal antibody having an antigen binding domain obtainable from a hybridoma deposited at the European Collection of Animal Cell Cultures (ECACC) under the accession number ECACC 95020716.

7. The method as claimed in claim 2 wherein said panel includes a monoclonal antibody comprising an antigen binding domain obtained from the hybridoma deposited under Accession Number ECACC 95020716.

* * * * *